United States Patent
Gilmore et al.

(10) Patent No.: US 7,875,666 B2
(45) Date of Patent: Jan. 25, 2011

(54) THIOETHERS, METHODS FOR THEIR PREPARATION, AND COMPOSITIONS INCLUDING SUCH THIOETHERS

(75) Inventors: John R. Gilmore, Valencia, CA (US); Chandra B. Rao, Valencia, CA (US)

(73) Assignee: PRC-De Soto International, Inc., Glendale, CA (US)

( * ) Notice: Subject to any disclaimer, the term of this patent is extended or adjusted under 35 U.S.C. 154(b) by 280 days.

(21) Appl. No.: 12/108,782

(22) Filed: Apr. 24, 2008

(65) Prior Publication Data

US 2009/0270554 A1 Oct. 29, 2009

(51) Int. Cl.
*C08K 5/36* (2006.01)

(52) U.S. Cl. .................... 524/392; 524/393; 568/39; 568/57; 568/59

(58) Field of Classification Search ............. 524/392, 524/393; 568/39, 57, 59
See application file for complete search history.

(56) References Cited

U.S. PATENT DOCUMENTS

| | | | |
|---|---|---|---|
| 2,466,963 A | 4/1949 | Patrick et al. | |
| 4,609,762 A | 9/1986 | Morris et al. | |
| 5,430,192 A | 7/1995 | Hobbs et al. | 568/22 |
| 5,912,319 A | 6/1999 | Zook et al. | |
| 5,959,071 A | 9/1999 | Demoss et al. | |
| 6,172,179 B1 | 1/2001 | Zook et al. | 528/373 |
| 6,486,297 B2 | 11/2002 | Zook et al. | 528/373 |
| 6,509,418 B1 | 1/2003 | Zook et al. | 525/212 |
| 6,525,168 B2 | 2/2003 | Zook et al. | 528/373 |
| 6,939,941 B2 | 9/2005 | Gilmore et al. | 528/389 |
| 7,009,032 B2 | 3/2006 | Bojkova et al. | 528/373 |
| 2005/0010003 A1 | 1/2005 | Sawant et al. | |

FOREIGN PATENT DOCUMENTS

| | | |
|---|---|---|
| EP | 0293117 A | 11/1988 |
| JP | 04046931 A | 2/1992 |
| WO | WO 2005/000965 A | 1/2005 |

OTHER PUBLICATIONS

Nuyken, Oskar et al., "Telechelics via addition of dithiols onto alkadienes, 1 Radical mechanism" Makromol Chem. Rapid Communications vol. 11, 1990 pp. 365-373 XP002539576.

Tenc-Popovic, Mirjana E. et al., "Synthesis of Disulfide Polymers of Low Molecular Weight Repeated Depolymerization" Journal of Polymer Sciense: Part A-1, vol. 10, 1972.

"Synthesis of Poly(aliphatic sulfides) by Polycondensation of Sodium Sulfide with Dibromoalkanes in the Presence of Quaternary Onium Salts" by Mitsuru Ueda et al., *Macromolecules* 1982, 15, pp. 248-251.

*Primary Examiner*—Edward J Cain
(74) *Attorney, Agent, or Firm*—Donald R. Palladino

(57) ABSTRACT

Disclosed are thioethers, methods for preparing such thioethers, and curable compositions, such as coating and sealant compositions, that include such thioethers. The thioethers can be the reaction product of (a) an alpha, omega dihalo organic compound, (b) a metal hydrosulfide, and (c) a metal hydroxide.

28 Claims, No Drawings

THIOETHERS, METHODS FOR THEIR PREPARATION, AND COMPOSITIONS INCLUDING SUCH THIOETHERS

FIELD OF THE INVENTION

The present invention is directed to thioethers, methods for preparing such thioethers, and curable compositions, such as coating and sealant compositions, that include such thioethers.

BACKGROUND OF THE INVENTION

Thiol-terminated sulfur-containing compounds are known to be well-suited for use in various applications, such as aerospace sealant compositions, due, in large part, to their fuel-resistant nature upon cross-linking. Other desirable properties for aerospace sealant compositions include low temperature flexibility, short curing time (the time required to reach a predetermined strength) and elevated-temperature resistance, among others. Sealant compositions exhibiting at least some of these characteristics and containing thiol-terminated sulfur-containing compounds are described in, for example, U.S. Pat. Nos. 2,466,963, 4,366,307, 4,609,762, 5,225,472, 5,912,319, 5,959,071, 6,172,179, 6,232,401, 6,372,849 and 6,509,418.

Polythioethers that are liquid at room temperature and pressure and have excellent low temperature flexibility and fuel resistance, such as are disclosed in U.S. Pat. No. 6,172,179, are often desired is aerospace sealant applications, for example. Unfortunately, such polythioethers can be relatively expensive to manufacture due to raw material costs, particularly certain polythiols from which such polythioethers are derived. As a result, it would be desirable to provide novel thioethers that exhibit acceptable, sometimes surprisingly excellent, properties, such as fuel-resistance and elevated-temperature resistance, as compared to those described in the prior art but that are capable of being produced without the use of a polythiol and, therefore, are capable of being produced at reduced cost as compared to polythioethers derived from certain polythiols.

The present invention has been developed in view of the foregoing.

SUMMARY OF THE INVENTION

In certain respects, the present invention is directed to thioethers. These thioethers of the present invention comprise the structure (I):

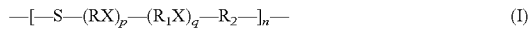
—[—S—(RX)$_p$—(R$_1$X)$_q$—R$_2$—]$_n$—  (I)

in which:
(a) each R, which may be the same or different, denotes a $C_{2-10}$ n-alkylene group, such as a $C_{2-6}$ n-alkylene group; a $C_{2-10}$ branched alkylene group, such as a $C_{2-6}$ branched or a $C_{3-6}$ branched alkylene group having one or more pendant groups which can be, for example, alkyl groups, such as methyl or ethyl groups; a $C_{6-8}$ cycloalkylene group; a $C_{6-14}$ alkylcycloalkylene, such as a $C_{6-10}$ alkylcycloalkylene group; or a $C_{8-10}$ alkylarylene group;
(b) each $R_1$, which may be the same or different, denotes a $C_{1-10}$ n-alkylene group, such as a $C_{1-6}$ n-alkylene group; a $C_{2-10}$ branched alkylene group, such as a $C_{2-6}$ or $C_{3-6}$ branched alkylene group having one or more pendant groups which can be, for example, alkyl groups, such as methyl or ethyl groups; a $C_{6-8}$ cycloalkylene group; a $C_{6-14}$ alkylcycloalkylene, such as a $C_{6-10}$ alkylcycloalkylene group; or a $C_{8-10}$ alkylarylene group;
(c) each $R_2$, which may be the same or different, denotes a $C_{2-10}$ n-alkylene group, such as a $C_{2-6}$ n-alkylene group; a $C_{2-10}$ branched alkylene group, such as a $C_{2-6}$ branched or a $C_{3-6}$ branched alkylene group having one or more pendant groups which can be, for example, alkyl groups, such as methyl or ethyl groups; a $C_{6-8}$ cycloalkylene group; a $C_{6-14}$ alkylcycloalkylene, such as a $C_{6-10}$ alkylcycloalkylene group; or a $C_{8-10}$ alkylarylene group;
(d) each X, which may be the same or different, denotes O, S, or N—$R_1$, wherein $R_1$ is as described above;
(e) p has a value of 1 to 5;
(f) q has a value of 0 to 5;
(g) n has a value of at least 1, such as at least 2, and in some cases 2 to 60, 3 to 60, or 25 to 35; and
(h) at least one, in some cases each, R and $R_1$ are different from each other.

In other respects, the present invention is directed to invention is directed to thioethers that comprise the structure (I), wherein:
(a) R denotes a $C_2$ n-alkylene group;
(b) $R_1$ denotes a $C_1$ n-alkylene group;
(c) $R_2$ denotes a $C_2$ n-alkylene group;
(d) X denotes O;
(e) p has a value of 1;
(f) q has a value of 1; and
(g) n has a value of at least 1, such as at least 2, and in some cases 2 to 60, 3 to 60, or 25 to 35.

In yet other respects, the present invention is directed to thioethers that are the reaction product of reactants comprising: (a) an alpha, omega dihalo organic compound, (b) a metal hydrosulfide, and (c) a metal hydroxide.

In still other respects, the present invention is directed to curable compositions, such as coating and sealant compositions, that comprise such thioethers.

The present invention is also directed to, inter alia, methods for making such thioethers.

DETAILED DESCRIPTION OF EMBODIMENTS OF THE INVENTION

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

As indicated, certain embodiments of the present invention are directed to thioethers. As used herein, the term "thioether" refers to compounds comprising at least one, often at least two thioether linkages; that is "—CH$_2$—S—CH$_2$—" linkages. In certain embodiments, such compounds are a polymer. As used herein, "polymer" refers to oligomers and both homopolymers and copolymers. Unless stated otherwise, if used herein, molecular weights are number average molecular weights for polymeric materials indicated as "Mn" and obtained by gel permeation chromatography using a polystyrene standard in an art-recognized manner.

Certain embodiments of the present invention are directed to thioethers that comprise a structure having the formula (I), described earlier. More particularly, with respect to formula (I), in certain embodiments: (a) each R, which may be the same or different, denotes a C$_{2-10}$ n-alkylene group, such as a C$_{2-6}$ n-alkylene group; (b) each R$_1$, which may be the same or different, denotes a C$_{1-10}$ n-alkylene group, such as a C$_{1-6}$ n-alkylene group; (c) each R$_2$, which may be the same or different denotes a C$_{2-10}$ n-alkylene group, such as a C$_{2-6}$ n-alkylene group; (d) each X denotes O; (e) p has a value of from 1 to 5; (f) q has a value of 0 to 5; (g) n has a value of at least 1, often at least two, such as 2 to 60, 3 to 60, or, in some cases 25 to 35; and (h) R and R$_1$ are different from each other. Furthermore, in certain embodiments, with respect to formula (I): (a) R denotes a C$_2$ n-alkylene group; (b) R$_1$ denotes a C$_1$ n-alkylene group; (c) R$_2$ denotes a C$_2$ n-alkylene group; (d) X denotes 0; (e) p has a value of 1; (f) q has a value of 1; and (g) n has a value of at least 1, often at least two, such as 2 to 60, 3 to 60, or, in some cases 25 to 35.

In certain embodiments, the thioethers of the present invention have a structure according to formula (II):

$$A\text{-}(\text{---}R^3)_2 \quad (II)$$

wherein: (a) A denotes a structure having the formula (I); and (b) each R$^3$, which may be the same or different, comprises —SH; —OH, alkyl, such as a C$_{1-10}$ n-alkyl group, alkylene, such as a C$_{1-10}$ n-alkylene group, —NCO,

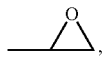

or a hydrolyzable functional group, such as a silane group, i.e.,

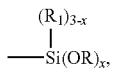

wherein R and R$_1$ each independently represent an organic group and x is 1, 2, or 3.

Thioethers in which R$^3$ is —SH are "uncapped," that is, include unreacted terminal thiol groups. Thioethers according to the invention also include "capped" thioethers, that is, thioethers including terminal groups other than unreacted thiol groups. These terminal groups can be, for example, any of the groups mentioned above, such as: (i) —OH, such as could be obtained by, for example, (a) reacting an uncapped thioether of the present invention with a monoxide, such as ethylene oxide, propylene oxide, and the like, in the presence of a base, or (b) reacting an uncapped thioether of the present invention with an olefinic alcohol, such as, for example, allyl alcohol, or a monovinylether of a diol, such as, for example, ethylene glycol monovinyl ether, propylene glycol monovinyl ether, and the like, in the presence of a free radical initiator; (ii) alkyl, such as could be obtained by reacting an uncapped thioether of the present invention with an alkylene; (iii) alkylene, such as could be obtained by reacting an uncapped thioether of the present invention with an diolefin; (iv) —NCO, such as could be obtained by reacting an uncapped thioether of the present invention with a polyisocyanate; (v)

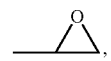

such as could be obtained by reacting an uncapped thioether of the present invention with a glycidylolefin; or (vi) a hydrolyzable functional group, such as could be obtained by reacting an uncapped thioether of the present invention with an olefinic alkoxysilane.

In certain embodiments, therefore, the thioether of the present invention is an uncapped thioether comprising the structure (III):

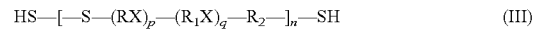

Certain embodiments of the present invention are directed to thioethers that comprise a structure having the formula (III), wherein: (a) each R, which may be the same or different, denotes a C$_{2-10}$ n-alkylene group, such as a C$_{2-6}$ n-alkylene group; (b) each R$_1$, which may be the same or different, denotes a C$_{1-10}$ n-alkylene group, such as a C$_{1-6}$ n-alkylene group; (c) each R$_2$, which may be the same or different denotes a C$_{2-10}$ n-alkylene group, such as a C$_{2-6}$ n-alkylene group; (d) each X denotes O; (e) p has a value of from 1 to 5; (f) q has a value of 0 to 5; (g) n has a value of at least 1, in some cases at least 2, such as 2 to 60, 3 to 60, or 25 to 35; and (h) R and R$_1$ are different from each other. Furthermore, in certain embodiments, with respect to formula (III): (a) R denotes a C$_2$ n-alkylene group; (b) R$_1$ denotes a C$_1$ n-alkylene group; (c) R$_2$ denotes a C$_2$ n-alkylene group; (d) X denotes O; (e) p has a value of 1; (f) q has a value of 1; and (g) n has a value of at least 1, in some cases at least 2, such as 2 to 60, 3 to 60, or 25 to 35.

In certain embodiments, the thioether of the present invention has the formula (IV):

$$B\text{-}(A\text{-}R_3)_z \quad (IV)$$

in which: (a) B denotes a z-valent residue of a polyfunctionalizing agent; (b) A denotes a structure having the formula (I); (c) each R$_3$, which may be the same or different, comprises —SH; —OH, alkyl, such as a C$_{1-10}$ n-alkyl group, alkylene, such as a C$_{1-10}$ n-alkylene group, —NCO,

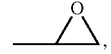

or a hydrolyzable functional group, such as a silane group, i.e.,

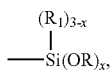

wherein R and $R_1$ each independently represent an organic group and x is 1, 2, or 3; and (d)

z is an integer from 3 to 6.

That is, the polyfunctionalized embodiments include three or more structures of the formula (I) bound to the residue of an appropriate polyfunctionalizing agent. In certain embodiments, z is 3, and the polyfunctionalizing agent thus is a trifunctionalizing agent. In other embodiments, the average functionality of the thioether ranges between about 2.05 and about 3.00.

In certain embodiments, the thioethers of the present invention are formed from reactants comprising, or, in some cases, consisting essentially of, or, in yet other cases, consisting of, (i) an alpha, omega dihalo organic compound, such as "x" moles thereof, (ii) a metal hydrosulfide, such as ≧2x moles thereof, (iii) a metal hydroxide, such as ≧2x moles thereof and optionally, (iv) a desired amount of polyfunctionalizing agent. In certain embodiments, the thioethers of the present invention are formed from reactants that are substantially free, or, in some cases, completely free, of any polythiol. As used herein, the term "substantially free" means that the material being discussed is present, if at all, as an incidental impurity. In other words, the material does not affect the properties of the thioether or the composition in which the thioether is used. As used herein, the term "completely free" means that the material being discussed is not present at all. In certain embodiments, the thioether of the present invention is produced by reacting the foregoing reactants in the presence of a phase transfer catalyst.

Suitable alpha, omega dihalo organic compounds have the chemical formula X—R—Y, where X and Y are halogens and R is an organic group. X and Y may be different halogen atoms or the same halogen atoms. By "alpha, omega" is meant that the halogen atoms are believed to be attached to opposite ends of the organic group. Suitable halogens include, for example, chlorine, bromine, and iodine. Suitable organic groups include, for example, alkyl groups with 3 or more carbon atoms, aryl groups, alkylaryl groups, alkoxy groups, and arylalkoxy groups. In certain embodiments, the organic group comprises an alkoxy group, specific examples of which can be illustrated by the chemical formulas (V) and (VI):

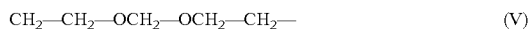 (V)

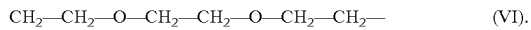 (VI).

In some embodiments, the organic group may comprise a sulfur atom, specific examples of which can be illustrated by the chemical formulas (VII) and (VIII):

 (VII)

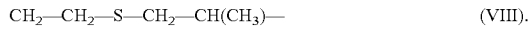 (VIII).

One specific example of an alpha, omega dihalo organic compound that is suitable for use in the present invention is bis(2-chloroethyl) formal.

Suitable metal hydrosulfides have the formula M-SH, where M is a metal. Specific examples of suitable metal hydrosulfides include, for example, sodium hydrosulfide, potassium hydrosulfide, lithium hydrosulfide, rubidium hydrosulfide, cesium hydrosulfide, as well as mixtures of two or more of the foregoing. These metal hydrosulfides can be used, for example, as hydrates, aqueous mixtures or anhydrous.

Suitable metal hydroxides have the formula $M\text{-}(OH)_x$, where M is a metal and x is 1, 2, or 3. Specific examples of suitable metal hydroxides include, for example, lithium hydroxide, sodium hydroxide, potassium hydroxide, calcium hydroxide, barium hydroxide, as well as mixtures of two or more of the foregoing. These metal hydroxides can be used, for example, as hydrates, aqueous mixtures or anhydrous.

Suitable phase transfer catalysts (PTCs) include, for example, quaternary ammonium salts, phosphonium salts, and crown ethers. A more detailed description of phase transfer catalysis and descriptions of compounds suitable as PTCs can be found in E. V. Dehmlow, "Catalysis, Phase Transfer," in volume 5 of the Kirk-Othmer Encyclopedia of Chemical Technology, 4th edition, Wiley (1996). Further examples of PTC's can be found in JP04046931, to T. Tozawa et. al. In certain embodiments of the present invention, the phase transfer catalyst comprises tetrabutylammonium bromide, 18-crown-6, tetraphenylphosphonium halide, and/or methyltributylammonium chloride. In certain embodiments, a suitable amount of PTC is 0.01 to 10 mole % based on the moles of the alpha, omega dihalo organic compound or compounds, such as 0.05 to 2.0 mole %.

As indicated, a polyfunctionalizing agent may also be used to prepare certain thioethers of the present invention, if desired. In these embodiments, suitable polyfunctionalizing agents include, for example, trihalo organic compounds, such as trihalo alkyl compounds, for example, trihalo propane. Suitable halogens again include, for example, chlorine, bromine, and iodine. In certain embodiments, the polyfunctionalizing agent comprises 1,2,3-trichloropropane, 1,1,1-tris(chloromethyl)propane, 1,1,1-tris(chloromethyl)ethane, and/or 1,3,5-tris(chloromethyl)benzene. In certain embodiments, a suitable amount of trihalo organic compound(s) is 0 to 10 moles of trihalo organic compound per 100 moles of alpha, omega dihalo organic compound(s), such as 1 to 5 moles of trihalo organic compound(s) per 100 moles of alpha, omega dihalo organic compound(s), or, in some cases 3 moles of trihalo organic compound(s) per 100 moles of alpha, omega dihalo organic compounds. The trihalo organic compound(s), if used, is often mixed with the alpha, omega dihalo organic compound(s) so that the mixed halo compounds are added together to the reaction mixture.

In certain embodiments, the thioether described above is a liquid at room temperature. Moreover, in certain embodiments, the previously described thioether has a viscosity, at 100% solids, of no more than 1500 poise, such as 40-500 poise, at a temperature of about 25° C. and a pressure of about 760 mm Hg determined according to ASTM D-2849 §79-90 using a Brookfield CAP 2000 viscometer. Any endpoint within the foregoing ranges can also be used.

As indicated, in certain embodiments, the thioether described above has a number average molecular weight of 300 to 10,000 grams per mole, such as 1,000 to 8,000 grams per mole, the molecular weight being determined by gel-permeation chromatography using a polystyrene standard. Any endpoints within the foregoing ranges can also be used.

In certain embodiments, the $T_g$ of the thioether of the present invention is not higher than −55° C., such as not higher than −60° C.

The Examples herein further illustrate suitable methods for making embodiments of the thioethers of the present invention.

As indicated, certain embodiments of the present invention are directed to compositions, such as sealant, coating, and/or electrical potting compositions that include the previously described thioethers. As used herein, the term "sealant composition" refers to a composition that is capable of producing a film that has the ability to resist atmospheric conditions, such as moisture and temperature and at least partially block the transmission of materials, such as water, fuel, and other liquid and gasses. In certain embodiments, the sealant compositions of the present invention are useful, e.g., as aerospace sealants and linings for fuel tanks. In certain embodiments, the composition comprises a thioether as described above; a curing agent; and a filler.

In certain embodiments, the compositions of the present invention comprise, in addition to a thioether as described earlier, one or more additional sulfur-containing polymers. As used herein, the term "sulfur-containing polymer" refers to any polymer having at least one sulfur atom, including, but not limited to, polymeric thiols, polythiols, thioethers, polythioethers and polysulfides. A "thiol", as used herein, refers to a compound comprising a thiol or mercaptan group, that is, an "SH" group, either as the sole functional group or in combination with other functional groups, such as hydroxyl groups, as is the case with, for example, thioglycerols. A "polythiol" refers to such a compound having more than one SH group, such as a dithiol or higher functionality thiol. Such groups are typically terminal and/or pendent such that they have an active hydrogen that is reactive with other functional groups. As used herein, the term "polysulfide" refers to any compound that comprises a sulfur-sulfur linkage (—S—S—). A "polythiol" can comprise both a terminal and/or pendant sulfur (—SH) and a non-reactive sulfur atom (—S— or (—S—S—)). Thus, the term "polythiol" generally encompasses "polythioether" and "polysulfide" as well. Suitable sulfur-containing polymers include, for example, those disclosed in U.S. Pat. Nos. 6,172,179, 6,509,418 and 7,009,032, incorporated by reference herein. Any sulfur-containing polymer used according to the present invention can further comprise additional functionality, including but not limited to hydroxyl functionality and epoxy functionality.

In certain embodiments, the thioether of the present invention is present in the composition of the present invention in an amount of at least 30 weight percent, such as least 40 weight percent, or, in some cases, at least 45 weight percent, based on the total weight of non-volatile components in the composition. In certain embodiments, the thioether of the present invention is present in the composition of the present invention in an amount of no more than 90 weight percent, such as no more than 80 weight percent, or, in some cases, no more than 75 weight percent, based on the weight of all non-volatile components of the composition.

As indicated, certain embodiments of the curable compositions of the present invention also comprise a curing agent. Curing agents useful in certain compositions of the invention include epoxy resins, for example, hydantoin diepoxide, diglycidyl ether of bisphenol-A, diglycidyl ether of bisphenol-F, Novolak type epoxides, and any of the epoxidized unsaturated and phenolic resins. Other useful curing agents include unsaturated compounds, such as acrylic and methacrylic esters of commercially available polyols, unsaturated synthetic or naturally occurring resin compounds, triallylcyanurate, and olefinic terminated derivatives of the compounds of the present invention.

Isocyanate functional compounds can also be useful curing agents in the compositions of the present invention. Suitable isocyanate functional compounds include, but are not limited to, polymeric polyisocyanates, non-limiting examples of which include polyisocyanates having backbone linkages chosen from urethane linkages (—NH(O)—O—), thiourethane linkages (—NH—C(O)—S—), thiocarbamate linkages (—NH—C(S)—O—), dithiourethane linkages (—NH—C(S)—S—) and combinations thereof.

The molecular weight of such a polymeric polyisocyanate can vary. In certain embodiments, the number average molecular weight (Mn) of each can be at least 100 grams/mole, or at least 150 grams/mole, or less than 15,000 grams/mole, or less than 5000 grams/mole. The number average molecular weight values recited herein can be determined by gel permeation chromatography (GPC) using polystyrene standards.

Non-limiting examples of suitable polyisocyanates, also include non-polymeric aliphatic polyisocyanates, cycloaliphatic polyisocyanates wherein one or more of the isocyanato groups are attached directly to the cycloaliphatic ring, cycloaliphatic polyisocyanates wherein one or more of the isocyanato groups are not attached directly to the cycloaliphatic ring, aromatic polyisocyanates wherein one or more of the isocyanato groups are attached directly to the aromatic ring, and aromatic polyisocyanates wherein one or more of the isocyanato groups are not attached directly to the aromatic ring.

In certain embodiments, the polyisocyanate includes, but is not limited to, aliphatic or cycloaliphatic diisocyanates, aromatic diisocyanates, cyclic dimers and cyclic trimers thereof, and mixtures thereof. Non-limiting examples of suitable polyisocyanates include, but are not limited to, Desmodur N 3300 (hexamethylene diisocyanate trimer) and Desmodur N 3400 (60% hexamethylene diisocyanate dimer and 40% hexamethylene diisocyanate trimer), which are commercially available from Bayer.

In certain embodiments, the polyisocyanate includes dicyclohexylmethane diisocyanate and/or isomeric mixtures thereof. As used herein, the term "isomeric mixtures" refers to a mixture of the cis-cis, trans-trans, and cis-trans isomers of the polyisocyanate. Non-limiting examples of isomeric mixtures for use in the present invention include the trans-trans isomer of 4,4'-methylenebis(cyclohexyl isocyanate), hereinafter referred to as "PICM" (paraisocyanato cyclohexylmethane), the cis-trans isomer of PICM, the cis-cis isomer of PICM, and mixtures thereof.

Three suitable isomers of 4,4'-methylenebis(cyclohexyl isocyanate) for use in the present invention are shown below.

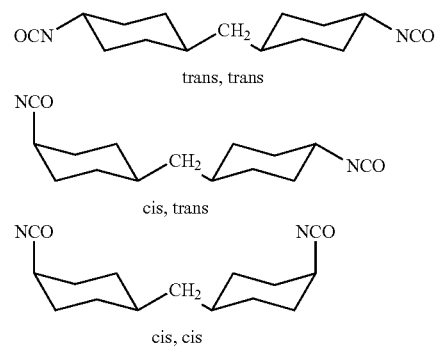

In certain embodiments, the isomeric mixture can contain from 10-100 percent of the trans,trans isomer of 4,4'-methylenebis(cyclohexyl isocyanate) (PICM).

Additional diisocyanates that can be used in certain embodiments of the present invention include 3-isocyanatomethyl-3,5,5-trimethyl cyclohexyl-isocyanate ("IPDI") and meta-tetramethylxylylene diisocyanate (1,3-bis(1-isocyanato-1-methylethyl)-benzene) which is commercially available from Cytec Industries Inc. under the tradename TMXDI® (Meta) Aliphatic Isocyanate.

As used herein, the terms aliphatic and cycloaliphatic diisocyanates refer to 6 to 100 carbon atoms linked in a straight chain or cyclized having two diisocyanate reactive end groups. In certain embodiments, the aliphatic and cycloaliphatic diisocyanates used in the present invention can include TMXDI and compounds of the formula R—(NCO)$_2$ wherein R represents an aliphatic group or a cycloaliphatic group.

Additional non-limiting examples of suitable polyisocyanates include, but are not limited to, ethylenically unsaturated polyisocyanates; alicyclic polyisocyanates; aromatic polyisocyanates wherein the isocyanate groups are not bonded directly to the aromatic ring, e.g., $\alpha,\alpha'$-xylylene diisocyanate; aromatic polyisocyanates wherein the isocyanate groups are bonded directly to the aromatic ring, e.g., benzene diisocyanate or methylene dibenzene diisocyanate, which has the structure

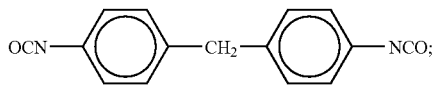

polyisocyanates containing sulfide and/or disulfide linkages; aromatic polyisocyanates containing sulfone linkages; sulfonic ester-type polyisocyanates, e.g., 4-methyl-3-isocyanatobenzenesulfonyl-4'-isocyanato-phenol ester; aromatic sulfonic amide-type polyisocyanates; sulfur-containing heterocyclic polyisocyanates, e.g., thiophene-2,5-diisocyanate; halogenated, alkylated, alkoxylated, nitrated, carbodiimide modified, urea modified and biuret modified derivatives of polyisocyanates thereof; and dimerized and trimerized products of polyisocyanates thereof.

In certain embodiments, a diisocyanate of the following structure can be used:

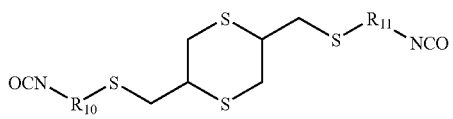

wherein $R_{10}$ and $R_{11}$ are each independently $C_1$ to $C_3$ alkyl.

Examples of suitable ethylenically unsaturated polyisocyanates include, but are not limited to, butene diisocyanate and 1,3-butadiene-1,4-diisocyanate.

Examples of suitable alicyclic polyisocyanates include, but are not limited to, isophorone diisocyanate, cyclohexane diisocyanate, methylcyclohexane diisocyanate, bis(isocyanatomethyl)cyclohexane, bis(isocyanatocyclohexyl)methane, bis(isocyanatocyclohexyl)-2,2-propane, bis(isocyanatocyclohexyl)-1,2-ethane, 2-isocyanatomethyl-3-(3-isocyanatopropyl)-5-isocyanatomethyl-bicyclo[2.2.1]-heptane, 2-isocyanatomethyl-3-(3-isocyanatopropyl)-6-isocyanatomethyl-bicyclo[2.2.1]-heptane, 2-isocyanatomethyl-2-(3-isocyanatopropyl)-5-isocyanatomethyl-bicyclo[2.2.1]-heptane, 2-isocyanatomethyl-2-(3-isocyanatopropyl)-6-isocyanatomethyl-bicyclo[2.2.1]-heptane, 2-isocyanatomethyl-3-(3-isocyanatopropyl)-6-(2-isocyanatoethyl)-bicyclo[2.2.1]-heptane, 2-isocyanatomethyl-2-(3-isocyanatopropyl)-5-(2-isocyanatoethyl)-bicyclo[2.2.1]-heptane and 2-isocyanatomethyl-2-(3-isocyanatopropyl)-6-(2-isocyanatoethyl)-bicyclo[2.2.1]-heptane.

Examples of suitable aromatic polyisocyanates wherein the isocyanate groups are not bonded directly to the aromatic ring also include, but are not limited to, bis(isocyanatoethyl)benzene, $\alpha,\alpha,\alpha',\alpha'$-tetramethylxylylene diisocyanate, 1,3-bis(1-isocyanato-1-methylethyl)benzene, bis(isocyanatobutyl)benzene, bis(isocyanatomethyl)naphthalene, bis(isocyanatomethyl)diphenyl ether, bis(isocyanatoethyl)phthalate, mesitylene triisocyanate and 2,5-di(isocyanato ethyl)furan, and meta-xylylene diisocyanate.

Examples of suitable aromatic polyisocyanates having isocyanate groups bonded directly to the aromatic ring also include, but are not limited to, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, naphthalene diisocyanate, methylnaphthalene diisocyanate, biphenyl diisocyanate, ortho-toluidine diisocyanate, ortho-tolylidine diisocyanate, ortho-tolylene diisocyanate, 4,4'-diphenylmethane diisocyanate, bis(3-methyl-4-isocyanatophenyl)methane, bis(isocyanatophenyl)ethylene, 3,3'-dimethoxy-biphenyl-4,4'-diisocyanate, triphenylmethane triisocyanate, polymeric 4,4'-diphenylmethane diisocyanate, naphthalene triisocyanate, diphenylmethane-2,4,4'-triisocyanate, 4-methyldiphenylmethane-3,5,2',4',6'-pentaisocyanate, diphenylether diisocyanate, bis(isocyanatophenylether)ethyleneglycol, bis(isocyanatophenylether)-1,3-propyleneglycol, benzophenone diisocyanate, carbazole diisocyanate, ethylcarbazole diisocyanate and dichlorocarbazole diisocyanate.

Examples of suitable aromatic polyisocyanates containing sulfide or disulfide linkages include, but are not limited to, diphenylsulfide-2,4'-diisocyanate, diphenylsulfide-4,4'-diisocyanate, 3,3'-dimethoxy-4,4'-diisocyanatodibenzyl thioether, bis(4-isocyanatomethylbenzene)-sulfide, diphenyldisulfide-4,4'-diisocyanate, 2,2'-dimethyldiphenyldisulfide-5,5'-diisocyanate, 3,3'-dimethyldiphenyldisulfide-5,5'-diisocyanate, 3,3'-dimethyldiphenyldisulfide-6,6'-diisocyanate, 4,4'-dimethyldiphenyldisulfide-5,5'-diisocyanate, 3,3'-dimethoxydiphenyldisulfide-4,4'-diisocyanate and 4,4'-dimethoxydiphenyldisulfide-3,3'-diisocyanate.

Examples of suitable aromatic polyisocyanates containing sulfone linkages also include, but are not limited to, diphenylsulfone-4,4'-diisocyanate, diphenylsulfone-3,3'-diisocyanate, benzidinesulfone-4,4'-diisocyanate, diphenylmethanesulfone-4,4'-diisocyanate, 4-methyldiphenylmethanesulfone-2,4'-diisocyanate, 4,4'-dimethoxydiphenylsulfone-3,3'-diisocyanate, 3,3'-dimethoxy-4,4'-diisocyanatodibenzylsulfone, 4,4'-dimethyldiphenylsulfone-3,3'-diisocyanate, 4,4'-di-tert-butyldiphenylsulfone-3,3'-diisocyanate and 4,4'-dichlorodiphenylsulfone-3,3'-diisocyanate.

Examples of suitable polyisocyanates include, but are not limited to, aromatic sulfonic amide-type polyisocyanates, such as 4-methyl-3-isocyanato-benzene-sulfonylanilide-3'-methyl-4'-isocyanate, dibenzenesulfonyl-ethylenediamine-4,4'-diisocyanate, 4,4'-methoxybenzenesulfonyl-ethylenediamine-3,3'-diisocyanate and 4-methyl-3-isocyanato-benzene-sulfonylanilide-4-ethyl-3'-isocyanate.

In addition, useful cures can be obtained through oxidative coupling of the thiol groups using organic and inorganic peroxides (e.g., $MnO_2$) known to those skilled in the art. Selection of the particular curing agent may affect the $T_g$ of the cured composition. For example, curing agents that have a $T_g$ significantly lower than the $T_g$ of the thioether(s) may lower the $T_g$ of the cured composition.

Depending on the nature of the thioether(s) used in the composition, the composition will often contain 90% to 150% of the stoichiometric amount, such as 95 to 125%, of the selected curing agent(s).

Fillers useful in the certain embodiments of the compositions of the present invention include those commonly used in the art, including conventional inorganic fillers, such as carbon black and calcium carbonate ($CaCO_3$), as well as lightweight fillers. Suitable lightweight fillers include, for example, those described in U.S. Pat. No. 6,525,168 at col. 4, lines 23-55, the cited portion of which being incorporated herein by reference. In certain embodiments, the compositions include 5 to 60 weight percent of the filler or combination of fillers, such as 10 to 50 weight percent, based on the total weight of the composition.

As will be appreciated, the thioethers, curing agents and fillers employed in certain compositions of the invention, as well as optional additives as described below, should be selected so as to be compatible with each other. Selection of compatible ingredients for the inventive compositions can readily be performed by those skilled in the art without recourse to undue experimentation.

In certain embodiments, the compositions of the present invention are curable at a minimum temperature of 0° C. (i.e., at a temperature of 0° C. or higher), such as −10° C., or, in some cases, −20° C., and have a $T_g$ when cured not higher than −55° C., such as not higher than −60° C., or, in some cases, not higher than −65° C.

In addition to the foregoing ingredients, certain compositions of the invention can optionally include one or more of the following: colorants; thixotropes; accelerators; retardants; adhesion promoters; solvents; and masking agents, among other components.

As used herein, the term "colorant" means any substance that imparts color and/or other opacity and/or other visual effect to the composition. The colorant can be added to the coating in any suitable form, such as discrete particles, dispersions, solutions and/or flakes. A single colorant or a mixture of two or more colorants can be used in the coatings of the present invention.

Example colorants include pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coatings by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), titanium dioxide, carbon black and mixtures thereof. The terms "pigment" and "colored filler" can be used interchangeably.

Example dyes include, but are not limited to, those that are solvent and/or aqueous based such as pthalo green or blue, iron oxide, bismuth vanadate, anthraquinone, perylene, aluminum and quinacridone.

Example tints include, but are not limited to, pigments dispersed in water-based or water miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemical, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800 B2, which is incorporated herein by reference. Nanoparticle dispersions can also be produced by crystallization, precipitation, gas phase condensation, and chemical attrition (i.e., partial dissolution). In order to minimize re-agglomeration of nanoparticles within the coating, a dispersion of resin-coated nanoparticles can be used. As used herein, a "dispersion of resin-coated nanoparticles" refers to a continuous phase in which is dispersed discreet "composite microparticles" that comprise a nanoparticle and a resin coating on the nanoparticle. Example dispersions of resin-coated nanoparticles and methods for making them are identified in United States Patent Application Publication 2005-0287348 A1, filed Jun. 24, 2004, U.S. Provisional Application No. 60/482,167 filed Jun. 24, 2003, and United States patent application Ser. No. 11/337,062, filed Jan. 20, 2006, which is also incorporated herein by reference.

Example special effect compositions that may be used in the compositions of the present invention include pigments and/or compositions that produce one or more appearance effects such as reflectance, pearlescence, metallic sheen, phosphorescence, fluorescence, photochromism, photosensitivity, thermochromism, goniochromism and/or colorchange. Additional special effect compositions can provide other perceptible properties, such as opacity or texture. In a non-limiting embodiment, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

In general, the colorant can be present in any amount sufficient to impart the desired visual and/or color effect. The colorant may comprise from 1 to 65 weight percent of the present compositions, such as from 3 to 40 weight percent or 5 to 35 weight percent, with weight percent based on the total weight of the compositions.

Thixotropes, for example silica, are often used in an amount from 0.1 to 5 weight percent, based on the total weight of the composition.

Cure catalysts known to the art, such as amines, often are present in an amount from 0.1 to 5 weight percent, based on the total weight of the composition. Specific examples of useful accelerators are, without limitation, 1,4-diaza-bicyclo [2.2.2]octane (DABCO®, commercially available from Air Products, Chemical Additives Division, Allentown, Pa.) and DMP-300 (an accelerant composition including 2,4,6-tris (dimethylaminomethyl)phenol, commercially available from Rohm and Haas. Philadelphia, Pa.). It has been surprisingly discovered, however, that certain embodiments of the present invention will cure at ambient conditions even in the absence of any such cure accelerator.

Retardants, such as stearic acid, likewise often are used in an amount from 0.1 to 5 weight percent, based on the total weight of the composition. Adhesion promoters, if employed, are often present in amount from 0.1 to 15 weight percent, based on the total weight of the composition. Suitable adhesion promoters include phenolics, such as METHYLON phenolic resin available from Occidental Chemicals, and organosilanes, such as epoxy, mercapto or amino functional silanes, such as A-187 and A-1100 available from OSi Specialties. Masking agents, such as pine fragrance or other scents, which are useful in covering any low level odor of the composition, are often present in an amount from 0.1 to 1 weight percent, based on the total weight of the composition.

In certain embodiments, the compositions of the present invention comprise a plasticizer which, in at least some cases, may allow the composition to include thioether(s) which have a higher $T_g$ than would ordinarily be useful in an aerospace sealant. That is, use of a plasticizer may effectively reduce the $T_g$ of the composition, and thus increase the low-temperature flexibility of the cured polymerizable composition beyond that which would be expected on the basis of the $T_g$ of the thioethers alone. Plasticizers that are useful in certain embodiments of the compositions of the present invention include, for example, phthalate esters, chlorinated paraffins, and hydrogenated terphenyls. The plasticizer or combination of plasticizers often constitute 1 to 40 weight percent, such as 1 to 10 weight percent of the composition. In certain embodiments, depending on the nature and amount of the plasticizer(s) used in the composition, thioethers of the invention which have $T_g$ values up to −50° C., such as up to −55° C., can be used.

In certain embodiments, the compositions of the present invention can further comprise one or more organic solvents, such as isopropyl alcohol, in an amount ranging from, for example, 0 to 15 percent by weight on a basis of total weight of the composition, such as less than 15 weight percent and, in some cases, less than 10 weight percent.

In certain embodiments, however, the compositions of the present invention are substantially free or, in some cases, completely free, of any solvent, such as an organic solvent or an aqueous solvent, i.e., water. Stated differently, in certain embodiments, the compositions of the present invention are substantially 100% active.

In certain embodiments, the compositions, such as the previously described sealant compositions, are embodied as multi-pack compositions, such as two-pack compositions, wherein one package comprises the previously described thioether polymer and the second pack comprises the curing agent. The previously described additives and other materials can be added to either package as desired or necessary. The two packages are simply mixed together at or near the time of use.

The compositions of the present invention can be applied to any of a variety of substrates. Common substrates to which the compositions of the present invention are applied can include titanium, stainless steel, aluminum, anodized, primed, organic coated and chromate coated forms thereof, epoxy, urethane, graphite, fiberglass composite, KEVLAR®, acrylics and polycarbonates.

The compositions of the present invention can be applied directly onto the surface of a substrate or over an underlayer by any suitable coating process known to those of ordinary skill in the art, for example, by extruding, dip coating, direct roll coating, reverse roll coating, curtain coating, spray coating, brush coating, vacuum coating and combinations thereof. The method and apparatus for applying the composition to the substrate may be determined, at least in part, by the configuration and type of substrate material.

In certain embodiments, the compositions of the present invention are fuel-resistant. As used herein, the term "fuel resistant" means that the compositions of the present invention, when applied to a substrate and cured, can provide a cured product, such as a sealant, that has a percent volume swell of not greater than 40%, in some cases not greater than 25%, in some cases not greater than 20%, in yet other cases not more than 10%, after immersion for one week at 140° F. (60° C.) and ambient pressure in jet reference fluid (JRF) type 1 according to methods similar to those described in ASTM D792 or AMS 3269, incorporated herein by reference. Jet reference fluid JRF type 1, as employed herein for determination of fuel resistance, has the following composition (see AMS 2629, issued Jul. 1, 1989), §3.1.1 et seq., available from SAE (Society of Automotive Engineers, Warrendale, Pa.) (that is incorporated herein by reference): herein by reference):

| | |
|---|---|
| Toluene | 28 ± 1% by volume |
| Cyclohexane (technical) | 34 ± 1% by volume |
| Isooctane | 38 ± 1% by volume |
| Tertiary dibutyl disulfide (doctor sweet) | 1 ± 0.005% by volume |

Indeed, it was a surprising discovery that certain embodiments of the present invention exhibit excellent fuel-resistance properties (percent volume swell of not greater than 10% as described above, which is often associated with polysulfides) as well as excellent elevated-temperature resistance (good tensile strength and elongation properties after 8 hours exposure at 360° F., which is often associated with polythioethers).

In certain embodiments, cured products, such as sealants, of the present invention have good low temperature flexibility as determined by known methods, for example, by the methods described in AMS (Aerospace Material Specification) 3267 §4.5.4.7, MIL-S (Military Specification)-8802E §3.3.12 and MIL-S-29574, and by methods similar to those described in ASTM (American Society for Testing and Materials) D522-88, which are incorporated herein by reference. Cured formulations having good low temperature flexibility are desirable in aerospace applications because the formulations are subjected to wide variations in environmental conditions, such as temperature and pressure, and physical conditions such as joint contraction and expansion and vibration.

In certain embodiments, compositions of the present invention also cure relatively quickly under ambient conditions. For example, in certain embodiments, the compositions provide a tack free film in no more than 1 hour, in some cases no more than ½ hour, after application and cure in ambient conditions. For purposes of the present invention tack free time is measured in accordance with the procedure described in AMS 3265B, §3.6.8, test procedure AS5127/1, §5.8.

In certain embodiments, sealant compositions of the present invention provide a cured product, such as a sealant, having an elongation of at least 100% and a tensile strength of at least 500 psi when measured in accordance with the procedure described in AMS 3279, §3.3.17.1, test procedure AS5127/1, §7.7.

In certain embodiments, sealant compositions of the present invention provide a cured product, such as a sealant having a lap shear strength of greater than 200 psi, in some cases at least 400 psi when measured according to the procedure described in BSS 7272.

As should be apparent from the foregoing description, the present invention is also directed to methods for sealing an aperture utilizing a composition of the present invention. These methods comprise (a) applying a composition of the present invention to a surface to seal the aperture; and (b) allowing the composition to cure under, for example, ambient conditions. As will also be appreciated, the present invention is also directed to aerospace vehicles comprising at least one surface coated with a coating composition of the present invention as well as aerospace vehicles comprising at least one aperture that is sealed with a sealant composition of the present invention.

Illustrating the invention are the following examples, which, however, are not to be considered as limiting the invention to their details. Unless otherwise indicated, all parts and percentages in the following examples, as well as throughout the specification, are by weight.

EXAMPLES

Example 1

Synthesis of Mercaptan-Capped Polythioether

Solid flakes of sodium hydrosulfide hydrate (834.04 g; purity: 70%; 10.42 moles) were charged into a 5 liter 4-neck flask followed by water (1.696 Kg). Flask was flushed with nitrogen and stirring was started. Freshly-prepared aqueous sodium hydroxide (306.18 g, concentration: 50%; 3.83 moles) was added into the solution of sodium hydrosulfide followed by phase transfer catalyst A-175 (14.06 g, 0.06 mole). Reaction mixture was heated to 160° F. A mixture of 2-chloroethylformal (748.89 g, 4.33 moles) and 1,2,3-trichloropropane (19.86 g, 0.13 mole) was added at 160-165° F. over 6.5 hr and stirring was continued for another 2 hr. Heating was continued at 175-180° F. for 8 hr and at 185-190° F. for 8 hr. Reaction mixture was cooled to ambient temperature. Partially-emulsified polymeric layer was separated and washed with five 400 ml portions of water. The last washing was free of sodium hydrosulfide as indicated by lead acetate paper test. Polymeric layer was then washed with acidified water (400 ml water containing 2 ml of 95% formic acid; ph: 2-3) and dissolved in 1.2 liter of chloroform. Organic portion was separated, filtered through a band of anhydrous sodium sulfate and concentrated to give 583 g of a off-white polymer; mercaptan equivalent weight: 1816 (iodine titration method); viscosity: 122P (spindle no. 6, @100 RPM; Brookfield Cap 2000 viscometer).

Example 2

Preparation of Sealant Formulation

Part A of the sealant formulation was prepared by mixing 59.9 parts by weight of the polythioether of Example 1, 39.0 parts by weight calcium carbonate, 0.6 parts by weight of titanium dioxide, and 0.5 parts by weight of 1,4-diaza-bicyclo [2.2.2]octane (DABCO®, commercially available from Air Products, Chemical Additives Division, Allentown, Pa.).

Part B of the sealant formulation was prepared by mixing 0.9 parts by weight of an epoxysilane adhesion promoter, 11.1 parts by weight HB-40 modified polyphenyl (commercially available from Solutia, Inc.); 41.6 parts by weight calcium carbonate; 46.2 parts by weight Epon 828 epoxy resin; and 0.2 parts by weight carbon black.

The sealant was made for testing by mixing 100 parts of Part A and 14 parts of Part B. A sealant prepared from the above composition exhibited the properties set forth in Table 1.

TABLE 1

Tested according to methods in SAE AS5127/1 (except as noted)

| Property | Result |
|---|---|
| Application Time | 2 hours |
| Tack Free Time | 4 hours |
| 24 hours hardness | 48 Shore A |
| 14 days Hardness | 52 Shore A |
| Volume swell- JRF Type 1 7 days @ 140° F. | 6% |
| Weight Loss- JRF Type 1 7 days @ 140° F. | 5% |
| Tensile & Elongation | |
| Standard Cure 7 days | 300 psi/400% |
| 7 days at 140° F. in JRF type I | 250 psi/400% |
| 8 hours @ 360° F. | 180 psi/130% |
| Adhesion | Tested on Mil C-27725 panel |
| Standard Cure 7 days | 43 pli 100% cohesive failure |
| 7 days at 140° F. in JRF type I | 35 pli 100% cohesive failure |

Whereas particular embodiments of this invention have been described above for purposes of illustration, it will be evident to those skilled in the art that numerous variations of the details of the present invention may be made without departing from the invention as defined in the appended claims.

We claim:

1. A compound comprising the structure:

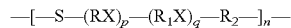

wherein:
   (a) R denotes a $C_{2-10}$ n-alkylene group; a $C_{3-10}$ branched alkylene group; a $C_{6-8}$ cycloalkylene group; a $C_{6-14}$ alkylcycloalkylene; or a $C_{8-10}$ alkylarylene group;
   (b) $R_1$ denotes a $CH_2$;
   (c) $R_2$ denotes a $C_{2-10}$ n-alkylene group; a $C_{3-10}$ branched alkylene group; a $C_{6-8}$ cycloalkylene group; a $C_{6-14}$ alkylcycloalkylene; or a $C_{8-10}$ alkylarylene group;
   (d) X denotes O or S;
   (e) p has a value of 1;
   (f) q has a value of 1; and
   (g) n has a value of at least 1.

2. The compound of claim 1, wherein n has a value of at least 2.

3. The compound of claim 2, wherein n has a value of no more than 60.

4. The compound of claim 3, wherein n has a value of 25 to 35.

5. The compound of claim 1, wherein the compound is the reaction product of reactants comprising:
   (a) an alpha, omega dihalo organic compound,
   (b) a metal hydrosulfide, and
   (c) a metal hydroxide.

6. The compound of claim 5, wherein the reactants further comprise:

(d) a polyfunctionalizing agent.

7. The compound of claim 5, wherein the reactants are substantially free of a polythiol.

8. The compound of claim 5, wherein the alpha, omega dihalo organic compound has the chemical formula X—R—Y, where X and Y are halogens and R is an organic group comprising an alkoxy group.

9. The compound of claim 8, wherein the alkoxy group comprises:

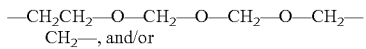

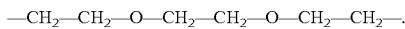

10. A composition comprising the compound of claim 1.

11. The composition of claim 10, wherein the composition is a sealant composition further comprising a curing agent and a filler.

12. A method for making a sulfur-containing compound, comprising reacting reactants comprising:

(a) an alpha, omega dihalo organic compound, (b) a metal hydrosulfide, and (c) a metal hydroxide, in the presence of a phase transfer catalyst.

13. The method of claim 12, wherein the reactants further comprise:

(d) a polyfunctionalizing agent.

14. The method of claim 12, wherein the reactants are substantially free of a polythiol.

15. The method of claim 12, wherein the alpha, omega dihalo organic compound has the chemical formula X—R—Y, where X and Y are halogens and R is an organic group comprising an alkoxy group.

16. The method of claim 15, wherein the alkoxy group comprises:

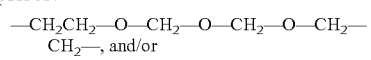

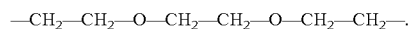

17. The composition of claim 11, further comprising an additional sulfur-containing polymer.

18. The composition of claim 17, wherein the additional sulfur-containing polymer comprises a polysulfide or a polythioether.

19. The compound of claim 6, wherein the polyfunctionalizing agent comprises a trihalo alkyl compound.

20. The method of claim 13, wherein the polyfunctionalizing agent comprises a trihalo alkyl compound.

21. A compound comprising the structure:

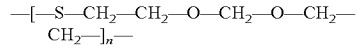

wherein n has a value of at least 1.

22. The compound of claim 21, wherein n has a value of at least 2.

23. The compound of claim 21, wherein n has a value of no more than 60.

24. The compound of claim 21, wherein n has a value of 25 to 35.

25. A composition comprising the compound of claim 21.

26. The composition of claim 25, wherein the composition is a sealant composition further comprising a curing agent and a filler.

27. The composition of claim 25, further comprising an additional sulfur-containing polymer.

28. The composition of claim 27, wherein the additional sulfur-containing polymer comprises a polysulfide or a polythioether.

* * * * *